(12) United States Patent
Morrow et al.

(10) Patent No.: US 7,010,433 B2
(45) Date of Patent: Mar. 7, 2006

(54) INDIRECT MEASUREMENT OF DILUENTS IN A MULTI-COMPONENT NATURAL GAS

(75) Inventors: Thomas B. Morrow, San Antonio, TX (US); Thomas E. Owen, Helotes, TX (US)

(73) Assignee: Southwest Research Institute, San Antonio, TX (US)

( * ) Notice: Subject to any disclaimer, the term of this patent is extended or adjusted under 35 U.S.C. 154(b) by 133 days.

(21) Appl. No.: 10/809,097

(22) Filed: Mar. 25, 2004

(65) Prior Publication Data

US 2004/0220751 A1 Nov. 4, 2004

Related U.S. Application Data

(60) Provisional application No. 60/458,049, filed on Mar. 27, 2003.

(51) Int. Cl.
*G01N 31/00* (2006.01)

(52) U.S. Cl. ............................. 702/24; 702/23; 702/50; 73/24.9

(58) Field of Classification Search .................... None
See application file for complete search history.

(56) References Cited

U.S. PATENT DOCUMENTS

| | | | | |
|---|---|---|---|---|
| 4,489,592 A | | 12/1984 | Pacanowski et al. ........... 73/30 |
| 4,596,133 A | | 6/1986 | Smalling et al. ............... 73/24 |
| 5,060,506 A | * | 10/1991 | Douglas ..................... 73/24.01 |
| 5,285,675 A | | 2/1994 | Colgate et al. ............... 73/23.2 |
| 5,311,447 A | | 5/1994 | Bonne ......................... 364/509 |
| 5,486,107 A | | 1/1996 | Bonne ......................... 431/12 |
| 5,537,854 A | * | 7/1996 | Phillips et al. ............. 73/24.01 |
| 5,932,793 A | | 8/1999 | Dayton et al. ............. 73/24.05 |
| 6,047,589 A | | 4/2000 | Hammond et al. ........ 73/24.01 |
| 6,065,328 A | | 5/2000 | Dayton et al. ............. 73/25.01 |
| 6,076,392 A | | 6/2000 | Drzewiecki ................. 73/23.2 |
| 6,209,387 B1 | | 4/2001 | Savidge ..................... 73/24.05 |
| 6,286,360 B1 | | 9/2001 | Drzewiecki ................ 73/24.01 |
| 6,704,660 B1 | | 3/2004 | Morrow et al. ............... 702/27 |
| 6,754,592 B1 | | 6/2004 | Morrow et al. ............... 702/27 |
| 2003/0212496 A1 | | 11/2003 | Morrow et al. ............... 702/24 |

FOREIGN PATENT DOCUMENTS

| | | |
|---|---|---|
| DE | 198 23 193 A1 | 11/1999 |
| EP | 1 063 525 A2 | 7/1999 |
| EP | 0 939 317 A2 | 9/1999 |
| EP | 0 959 354 A2 | 11/1999 |
| WO | 93/08457 | 4/1993 |
| WO | 99/10740 | 3/1999 |

OTHER PUBLICATIONS

International Search Report PCT/US01/12217, Nov. 13, 2001.

(Continued)

*Primary Examiner*—Michael Nghiem
*Assistant Examiner*—Stephen J. Cherry
(74) *Attorney, Agent, or Firm*—Baker Botts L.L.P.

(57) ABSTRACT

A method of indirectly measuring the diluent (nitrogen and carbon dioxide) concentrations in a natural gas mixture. The molecular weight of the gas is modeled as a function of the speed of sound in the gas, the diluent concentrations in the gas, and constant values, resulting in a model equation. A set of reference gas mixtures with known molecular weights and diluent concentrations is used to calculate the constant values. For the gas in question, if the speed of sound in the gas is measured at three states, the three resulting expressions of molecular weight can be solved for the nitrogen and carbon dioxide concentrations in the gas mixture.

15 Claims, 2 Drawing Sheets

OTHER PUBLICATIONS

International Preliminary Examination Report PCT/US01/12217, Jul. 8, 2002.

Wild, K.R., "Controlling Processes that are Sensitive to Natural Gas Quality", presented at the 21st World Gas Conference, Nice France, Jun. 6-9, 2000.

* cited by examiner

| GAS MIXTURE CHARACTERISTIC | RANGE OF GAS MIXTURE CHARACTERISTIC |
|---|---|
| MOLECULAR WEIGHT, $M$ [LBM/LB-MOL] | 16.33 - 19.52 |
| IDEAL SPECIFIC GRAVITY, $G_{id}$ [$M$/28.9625] | 0.564 - 0.674 |
| STANDARD VOLUMETRIC HEATING VALUE $H_{v,std}$ [BTU/REAL SCF AT 60°F, 14.73 PSIA] | 987 - 1150 |
| $C_6+$ CONCENTRATION [mol %] | 0.0009 - 0.100 |
| TOTAL DILUENT CONCENTRATION [mol %] | 0.968 - 7.40 |
| METHANE [mol %] | 83.42 - 98.27 |
| ETHANE [mol %] | 0.516 - 9.53 |
| PROPANE [mol %] | 0.161 - 3.57 |
| ISO-BUTANE [mol %] | 0.0355 - 0.647 |
| N-BUTANE [mol %] | 0.0237 - 0.432 |
| ISO-PENTANE [mol %] | 0.0094 - 0.167 |
| N-PENTANE [mol %] | 0.0063 - 0.112 |
| N-HEXANE [mol %] | 0.0003 - 0.0654 |
| N-HEPTANE [mol %] | 0.0000 - 0.0260 |
| N-OCTANE [mol %] | 0.0000 - 0.0235 |
| CARBON DIOXIDE [mol %] | 0.0330 - 6.00 |
| NITROGEN [mol %] | 0.0330 - 6.00 |

*FIG. 1*

INDIRECT MEASUREMENT OF DILUENTS IN A MULTI-COMPONENT NATURAL GAS

RELATED PATENT APPLICATION

This application claims the benefit of U.S. Provisional Application No. 60/458,049, filed Mar. 27, 2003 and entitled "Indirect Measurement of Diluents in a Multi-Component Natural Gas".

GOVERNMENT LICENSE RIGHTS

The U.S. Government has a paid-up license in this invention and the right in certain circumstances to require the patent owner to license others on reasonable terms as provided for by the terms of Contract No. DE-FC21-96MC33033 for the U.S. Department of Energy.

FIELD OF THE INVENTION

This invention relates to the field of measuring constituent components of gas mixtures, and more particularly, to measuring the concentration of diluents in a natural gas mixture.

DESCRIPTION OF THE RELATED ART

The concentration of nitrogen in a gas mixture is difficult to measure directly. Nitrogen has low infrared absorption characteristics, which makes infrared sensing methods difficult. Also, it is chemically inert, which makes electrochemical sensing methods difficult.

Yet, it is often desired to determine the amount of nitrogen in a particular gas mixture. For example, in a natural gas, nitrogen is a diluent and the amount of nitrogen affects heating value. Experimentation has indicated that a plus or minus shift of 0.075 mole % in nitrogen concentration will produce a plus or minus shift of 1.0 BTU/SCF in standard volumetric heating value.

U.S. Pat. No. 6,604,051 B1, entitled "System and Method to Determine Thermophysical Properties of a Multi-Component Gas" and U.S. Pat. No. 6,704,660 entitled "A System and Method to Determine Thermophysical Properties of a Multi-Component Gas at Arbitrary Temperature and Pressure", to K. Behring and T. Morrow, describe inferential methods for deriving the heating value of natural gas. These methods developed from correlation studies of the heating value of a large number of representative samples of natural gas and three independent physical parameters associated with the gas, namely, the speed of sound at specified pressure and temperature and the fractional concentrations of two diluent gas components (carbon dioxide and molecular nitrogen).

U.S. Pat. No. 6,604,051 B1 further describes various methods for determining the amount of molecular nitrogen in a natural gas sample. These methods are inferential in nature in that the concentration of nitrogen in representative natural gas mixtures, like the gas heating value, is correlated with the speed of sound and the carbon dioxide concentration at two independent thermodynamic states. Inferential nitrogen measurement techniques are further described in U.S. patent application Ser. No. 10/460,579, entitled "Indirect Measurement of Nitrogen in a Multi-Component Natural Gas by Heating the Gas" and in U.S. patent application Ser. No. 10/401,206, entitled "Indirect Measurement of Nitrogen in a Multi-Component Gas by Measuring the Speed of Sound at Two States of the Gas" filed Mar. 27, 2003, both continuations-in-part of U.S. Pat. No. 6,604,051 B1.

BRIEF DESCRIPTION OF THE FIGURES

FIG. 1 illustrates the characteristics of an example of a database for correlating molecular weight of natural gas to the speed of sound in the gas.

DETAILED DESCRIPTION OF THE PREFERRED EMBODIMENT

Figure 2:
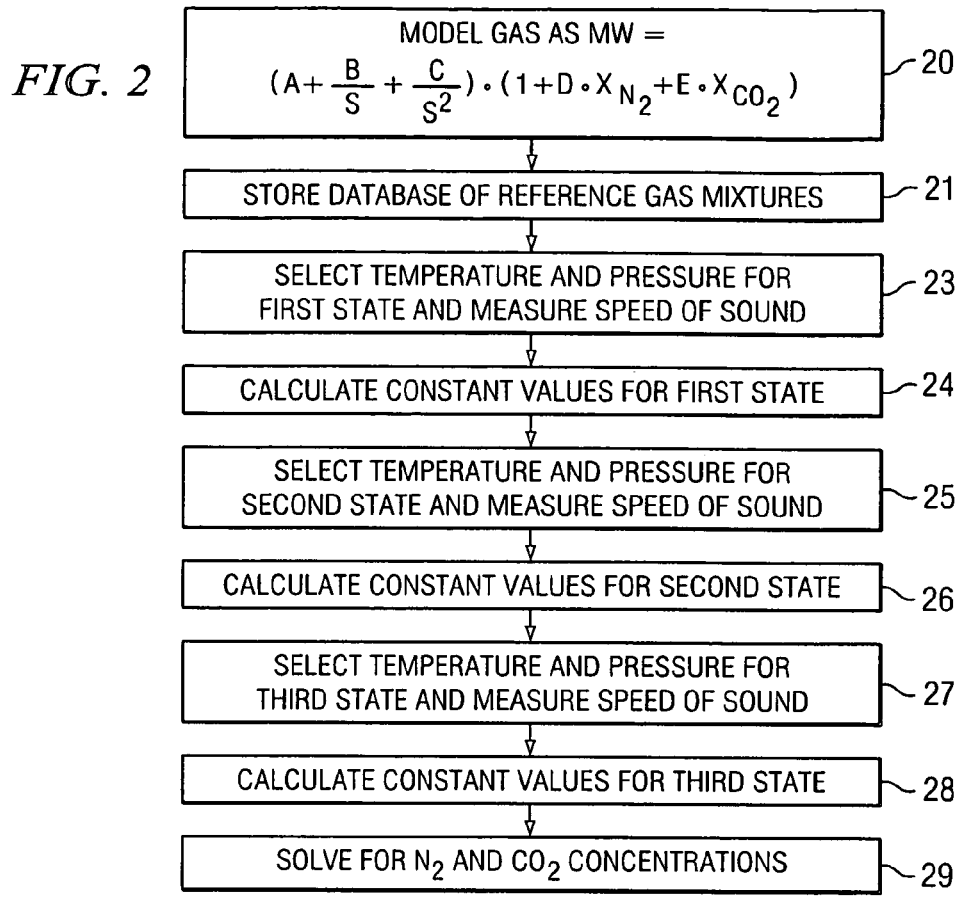
FIG. 2 illustrates a method of determining the diluent concentrations in a gas mixture in accordance with the invention.

As stated in the Background, U.S. Pat. No. 6,604,051 B1, entitled "System and Method to Determine Thermophysical Properties of a Multi-Component Gas" and U.S. Pat. No. 6,704,660 entitled "A System and Method to Determine Thermophysical Properties of a Multi-Component Gas at Arbitrary Temperature and Pressure", describe methods for inferentially measuring heating value and energy flow rates of natural gas. U.S. Pat. No. 6,604,051 B1 further describes methods for inferentially measuring nitrogen. The nitrogen measurement methods are further described in U.S. patent application Ser. No. 10/371,419, entitled "Indirect Measurement of Nitrogen in a Multi-Component Natural Gas by Heating the Gas" and in U.S. patent application Ser. No. 10/401,206, entitled "Indirect Measurement of Nitrogen in a Multi-Component Gas by Measuring the Speed of Sound at Two States of the Gas" filed Mar. 27, 2003. These patent applications are incorporated by reference herein.

Two-State Nitrogen Measurement

For inferentially measuring nitrogen, two thermodynamic states may be established by changing the energy status of the test gas from a first state, at a stable and measured temperature and pressure condition, to a second stable and measurable temperature and pressure condition. The measured physical parameters include the pressure at the two states, the temperature at the two states, the speed of sound at the two states, and the carbon dioxide concentration at either state.

As explained below, with a sufficient change in state of the gas, the correlation relationships regarding the nitrogen content are sufficiently independent to yield a quantitative determination of the concentration of nitrogen in the test sample.

For purposes of this description, the gas mixture is assumed to be a natural gas, whose primary diluent components are carbon dioxide and nitrogen. The method is most accurate when the concentration of other diluent gases is low. The method described herein may be extended to other gases containing nitrogen, if those gases behave similarly to natural gases.

For the "two-state" inferential measurement of nitrogen, it is assumed that for the particular gas mixture in question, the speed of sound in the gas and the concentration of carbon dioxide are known or measurable by direct or indirect measurement. The variables, $X_{CO2}$, $X_{N2}$, and S represent the carbon dioxide concentration, nitrogen concentration, and speed of sound in the gas, respectively. Temperature and pressure of the gas are represented by T and P. Typically, these measurements are made using a finite gas sample.

The molecular weight of a natural gas mixture of unknown composition is constant for the specific mixture. However, the molecular weight is quantitatively unknown because the gas constituents are not known.

As explained in U.S. Pat. No. 6,604,051 B1, molecular weight of a gas mixture plots semi-linear with sound speed, with the scatter in the data (about 1%) being a function of the diluent concentrations. Molecular weight (MW) may be represented by the following equation, which relates molecular weight to speed of sound and the diluent gas concentrations:

$$MW=(A+B/S+C/S^2)*(1+D*X_{CO2}+E*X_{N2}),\quad [1]$$

where MW is the molecular weight of a gas sample.

The constants A, B, C, D, and E are derived from a database containing reference gas mixtures, whose molecular weights are known. These constants are functions of the gas temperature and pressure, but they are not functions of the gas composition.

FIG. 1 summarizes a database composition range for a set of reference gas compositions. U.S. Pat. No. 6,604,051 B1, incorporated by reference above, provides an example of a suitable database, representing 102 unique gas compositions that fall within these ranges. For each reference gas mixture, the speed of sound can be calculated for a matrix of temperature and pressure values. The speed of sound calculations may be performed using commercially available computer software such as SONICWARE, manufactured by Lomic, Inc. By applying statistical methods to the database, values of the constants can be calculated for any given temperature and pressure state.

The database for producing the constant values may also comprise a smaller set of reference gas compositions, selected to be representative of different molecular weights and diluent concentrations. For example, a database of nine reference gas mixtures might comprise three categories of mixtures, one with high molecular weight, one with intermediate molecular weight, and one with low molecular weight. Each category could then comprise three mixtures, such as, one with no diluents, one with nitrogen as the only diluent, and one with carbon dioxide as the only diluent. An example of a suitable diluent concentration for this database would be 2.0 mole % of either nitrogen or carbon dioxide or both. Once a suitable set of reference gases is selected, standard matrix operations for solving algebraic equations can be used to produce values for the constants. For example, the database might comprise nine reference gases, each having a unique value of molecular weight. The sound speeds for each of the nine gases for a range of discrete temperature and pressure values is calculated and stored. As stated above, this calculation can be performed using commercially available software. Then, once the temperature and pressure of the subject natural gas is measured, interpolation can be used to estimate the speed of sound at that state for the reference gases. With nine values of sound speed, nine values of molecular weight, and nine values of CO2 and N2 for the nine reference gases, there is sufficient information to find the values of A, B, C, D and E at that state. As an alternative to storing pre-calculated sound speed values, the sound speeds for the reference gases could be calculated "on the fly" for the measured temperature and pressure, if appropriate programming is incorporated into the run time calculations.

The relations between the molecular weight (MW), the diluent gas concentrations ($X_{N2}$ and $X_{CO2}$), and the speed of sound (S) is, for a first thermodynamic state ($P_1$ and $T_1$):

$$MW = \left(A_1 + \frac{B_1}{S_1} + \frac{C_1}{S_1^2}\right)(1 + D_2 X_{CO2} + E_2 X_{N2}) \quad [2]$$

If the speed of sound measurement is repeated at an additional and different pressure and temperature condition, the corresponding molecular weight expression at $P_2$ and $T_2$ is:

$$MW = \left(A_2 + \frac{B_2}{S_2} + \frac{C_2}{S_2^2}\right)(1 + D_2 X_{CO2} + E_2 X_{N2}) \quad [3]$$

The second speed of sound measurement can be at a different pressure or temperature or both, as compared to the first speed of sound measurement. A change in either temperature or pressure or both fulfills the requirement that a measurement be made at a different thermodynamic state. If the two states are too close together, especially in pressure, the constants become closer in value and the nitrogen value less determinate.

One of the speed of sound measurements can be at standard temperature and pressure. This speed of sound measurement is referred to as the "standard sound speed", where standard temperature is 60° F. and standard pressure is 14.73 psia.

For sufficiently accurate and independent measurements of the speed of sound values, $S_1$, and $S_2$, Equations [2] and [3] may be equated to eliminate molecular weight and to solve for the concentration of nitrogen, $X_{N2}$, in terms of the carbon dioxide concentration, $X_{CO2}$, $$X_{N2} = \frac{\left(A_2 + \frac{B_2}{S_2} + \frac{C_2}{S_2^2}\right)(1 + D_2 X_{CO2}) - \left(A_1 + \frac{B_1}{S_1} + \frac{C_1}{S_1^2}\right)(1 + D_1 X_{CO2})}{E_1\left(A_1 + \frac{B_1}{S_1} + \frac{C_1}{S_1^2}\right) - E_2\left(A_2 + \frac{B_2}{S_2} + \frac{C_2}{S_2^2}\right)} \quad [4]$$

The separate measurement of the carbon dioxide concentration, obtained from the gas sample at either one of the test states, may now be substituted into the above equation to obtain the molecular nitrogen concentration, $X_{N2}$.

Three-State Diluent Measurement

By supplementing the two-state measurement method with a third state measurement, the need for measuring the carbon dioxide concentration in the test gas sample is eliminated. Three equations for molecular weight are obtained, and can be solved for both diluent concentrations (nitrogen and carbon dioxide).

FIG. 2 illustrates this "three-state" method of determining the diluent concentrations in a sample of natural gas. Step 20 is storing a database representing a number of gas mixtures whose molecular weights and diluent constituents are known. Step 21 is modeling molecular weight of any gas mixture as a function of the speed of sound in the gas, as described above.

Step 23 is measuring the speed of sound in the gas mixture at a first pressure and temperature. At that state, the equation for molecular weight is:

$$MW=(A_1+B_1/S_1+C_1/S_1^2)*(1+D_1*X_{N2}+E_1*X_{CO2}) \quad [5]$$

In Step 24, values for the constants ($A_1$, $B_1$, ...) are calculated, using the reference gas data, which includes sound speed values at the pressure and temperature of this first state, using the techniques described above.

In Step 25, the speed of sound measurement is then repeated at a different state. The molecular weight is then expressed as:

$$MW = (A_2 + B_2/S_2 + C_2/S_2^2)*(1 + D_2*X_{N2} + E_2*X_{CO2}) \quad [6]$$

Step 26 is calculating the constants ($A_2$, $B_2$, ...), to obtain a new set of constant values at that state.

Step 27 is repeating the speed of sound measurement at a third thermodynamic state, $P_3$, $T_3$, to yield a third independent molecular weight expression:

$$MW = (A_3 + B_3/S_3 + C_3/S_3^2)*(1 + D_3*X_{N2} + E_3*X_{CO2}) \quad [7]$$

Step 28 is calculating the constants ($A_3$, $B_3$, ...), to obtain a new set of constant values at the third state.

Step 29 is using the three molecular weight equations to solve for the diluent concentrations. Equations [5] and [6] may be equated to eliminate molecular weight and to solve for the concentration of nitrogen, $X_{N2}$, in terms of the carbon dioxide concentration.

$$X_{N2} = \frac{\left(A_2 + \frac{B_2}{S_2} + \frac{C_2}{S_2^2}\right)(1 + D_2 X_{CO2}) - \left(A_1 + \frac{B_1}{S_1} + \frac{C_1}{S_1^2}\right)(1 + D_1 X_{CO2})}{E_1\left(A_1 + \frac{B_1}{S_1} + \frac{C_1}{S_1^2}\right) - E_2\left(A_2 + \frac{B_2}{S_2} + \frac{C_2}{S_2^2}\right)} \quad [8]$$

Similarly, Equations [6] and [7] may be equated to eliminate molecular weight and obtain a second equation for nitrogen concentration:

$$X_{N2} = \frac{\left(A_3 + \frac{B_3}{S_3} + \frac{C_3}{S_3^2}\right)(1 + D_3 X_{CO2}) - \left(A_2 + \frac{B_2}{S_2} + \frac{C_2}{S_2^2}\right)(1 + D_2 X_{CO2})}{E_2\left(A_2 + \frac{B_2}{S_2} + \frac{C_2}{S_2^2}\right) - E_3\left(A_3 + \frac{B_3}{S_3} + \frac{C_3}{S_3^2}\right)} \quad [9]$$

Then, by eliminating $X_{N2}$ in the two preceding equations, the carbon dioxide concentration, $X_{CO2}$, may be expressed in terms of the three measured speeds of sound. That is, the carbon dioxide concentration is expressed as:

$$X_{CO2} = \frac{\begin{bmatrix}\left(A_1 + \frac{B_1}{S_1} + \frac{C_1}{S_1^2}\right)\left(A_2 + \frac{B_2}{S_2} + \frac{C_2}{S_2^2}\right)(E_2 - E_1) + \\ \left(A_3 + \frac{B_3}{S_3} + \frac{C_3}{S_3^2}\right)(E_1 - E_3)\right] + \left(A_2 + \frac{B_2}{S_2} + \frac{C_2}{S_2^2}\right) \\ \left(A_3 + \frac{B_3}{S_3} + \frac{C_3}{S_3^2}\right)(E_3 - E_2)\end{bmatrix}}{\begin{bmatrix}\left(A_1 + \frac{B_1}{S_1} + \frac{C_1}{S_1^2}\right)\left(A_2 + \frac{B_2}{S_2} + \frac{C_2}{S_2^2}\right)(E_1 D_2 - E_2 D_1) + \\ \left(A_3 + \frac{B_3}{S_3} + \frac{C_3}{S_3^2}\right)(E_3 D_1 - E_1 D_3)\right] + \left(A_2 + \frac{B_2}{S_2} + \frac{C_2}{S_2^2}\right) \\ \left(A_3 + \frac{B_3}{S_3} + \frac{C_3}{S_3^2}\right)(E_2 D_3 - E_3 D_2)\end{bmatrix}} \quad [10]$$

The value of $X_{CO2}$ may then be calculated, using the calculated constant values and the three measured values of speed of sound. This value may then be substituted into either of the nitrogen equations to obtain the value of $X_{N2}$. Then, the values of $X_{CO2}$ and $X_{N2}$ may be substituted into Equation [1], [2] or [3] to obtain the value of the test gas molecular weight, MW.

Diluent Measurement System

Figure 3:
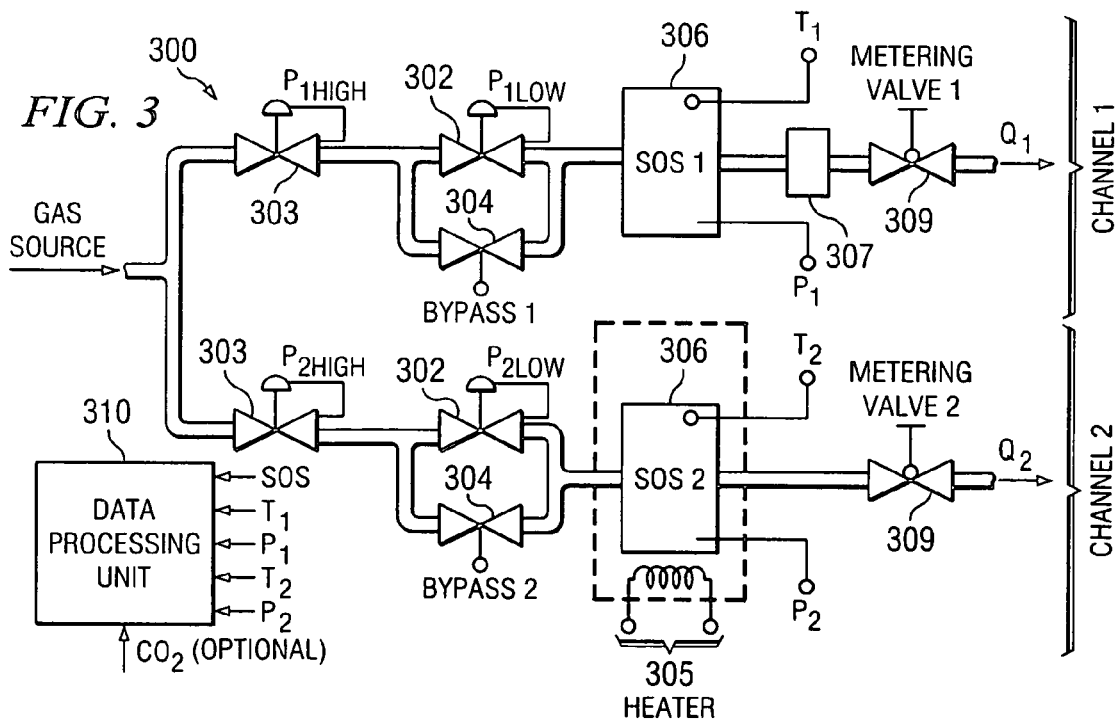
FIG. 3 illustrates a two-channel diluent measurement system in accordance with the invention.

FIG. 3 illustrates a two-channel diluent measurement system 300, with which up to four different speed of sound measurements at predetermined and measurable pressures and temperatures may be obtained. System 300 uses two speed of sound sensors 306, one on each of two channels. On each channel, two cascaded pressure regulator valves 302 and 303 and a switched bypass valve 304 are used to change the pressure in the channel.

Each channel operates independently at two different selectable pressures from a common gas supply source. On each channel, the selectable pressures are preset by the two pressure regulator valves 302 and 303 arranged in cascade with the lower pressure regulator 302, located downstream of the higher pressure regulator 303, shunted by a solenoid-operated bypass valve 304. With this arrangement, the pressure conditions in each measurement channel can be quickly and automatically changed from high to low pressure and vice versa, without interaction between the two channels.

One of the measurement channels (Channel 1) operates at the system ambient temperature. The other channel (Channel 2) has an electric heater 305 as part of the speed of sound test chamber 306 to raise the temperature of the gas in that chamber above the system ambient temperature.

An example of a suitable speed of sound sensor 306 is described in U.S. patent application Ser. No. 10/406,518, entitled "Device for Precision Measurement of Speed of Sound in a Gas" and incorporated by reference herein. The speed of sound sensor described therein has a self-contained capillary flow channel made as an intimate part of the chamber for the purpose of equilibrating the gas temperature to that of the chamber prior to measuring the speed of sound.

Both channels of system 300 may be operated with gas flowing through the speed of sound sensors 306, provided that the flow rate does not prevent the gas temperature from equilibrating to the chamber temperature. If a carbon dioxide sensor 307 is desired, it may be located at the exit metering valve 309 of the ambient-temperature speed of sound test channel.

The pressure and temperature test conditions in each measurement channel are relatively arbitrary, but are within the limits for reliable measurement of speed of sound (typically above a few atmospheres pressure or higher). The pressure and temperature values also are sufficiently different to provide adequate differences among the two (or three or four) thermodynamic states used in the test measurements in order to provide distinctive and independent results in the measured speed of sound values and in the subsequent calculations of the diluent gas concentrations and molecular weight. The temperatures in the measurement channels may likewise be relatively arbitrary provided that the heated channel temperature is sufficiently higher than the ambient temperature channel so as to have an independent influence on the measured speeds of sound. The temperatures in the two measuring channels may actually change with time to track any changing ambient temperature conditions caused by variations in environmental temperature at the system installation.

Examples of suitable pressures and temperature ranges for the two measurement channels are:

| Channel No. 1: | Channel No. 2: |
|---|---|
| 75 psia < $P_1$ < 1400 psia | 75 psia < $P_2$ < 1400 psia |
| deg F. < $T_1$ = $T_{amb}$ < 120 deg F. | $T_2$ = $T_{amb}$ + 40 deg F. |

An advantage of the three-state measurement method is that the sensing requirements only involve the measurement of speed of sound at the various preset and accurately measured pressures and temperatures. No other gas sensors are required and the amount of heat energy added to the gas in the heated channel is not required to be known. Likewise, the gas flow rates in the two measuring channels, although preferably set to be approximately equal, may be different from one another and are not required to be known.

Processing unit 310 receives speed of sound, temperature, and pressure measurement from the corresponding sensors of FIG. 3. These inputs are used to calculate only nitrogen or both nitrogen and carbon dioxide concentrations, in accordance with the two-state or three-state methods described above. Processing unit 310 is programmed in accordance with the methods described above. For determining the constant values, processing unit 310 may include a look up table of reference gases and pre-calculated sound speed values as described above, so that the constant values may be determined. Alternatively, processing unit 310 may include stored reference gas compositions and programming for determining sound speed values for the reference gases at the measured temperature and pressure, so that the constants may be determined.

If the three-state inferential method does not provide sufficient accuracy in resolving the individual concentrations of the carbon dioxide and molecular nitrogen diluent gases, carbon dioxide sensor 307 may be used to constrain the concentration, $X_{CO2}$, as a means for determining the concentration of molecular nitrogen, $X_{N2}$, with acceptable accuracy. In this case, the speed of sound measurements are required at only two independent energy states in the test gas sample.

The methods described above take the two diluent gases into separate consideration in order to develop the underlying principles for measurements that potentially do not require a measurement of carbon dioxide. If the two diluent gases are not accurately separable by these relationships, substituting a measured value of $X_{CO2}$ into either of the nitrogen equations to obtain the concentration of molecular nitrogen, $X_{N2}$, may not yield a suitably accurate result. In that case, an alternate approach is to reformat Equations [1], [2], and [3], with $X_{CO2}$ and $X_{N2}$ merged into a single "combined" diluent gas parameter, $X_{DIL}$, which represents the total diluent gas concentration. By eliminating MW among the equations as before, a value for $X_{DIL}$ can be obtained. Subtracting the measured value of $X_{CO2}$ from $X_{DIL}$ will yield the concentration of molecular nitrogen, $X_{N2}$, with a derived value potentially more accurate than that obtainable with the diluent concentration formulas involving separate gas constituent terms.

What is claimed is:

1. A method of determining the diluent concentrations in a natural gas, comprising the steps of:

storing a database representing a number of reference natural gas mixtures whose molecular weights and carbon dioxide and nitrogen concentrations are known;

modeling the molecular weight of a gas mixture as a function of the speed of sound in the gas mixture, the carbon dioxide concentration, the nitrogen concentration, and a set of constant values, thereby obtaining a model equation;

at a first temperature and pressure state of the gas mixture: measuring the speed of sound in the gas mixture, determining the constant values for the gas mixture from the database, and substituting these values into the model equation, thereby obtaining a first equation for the molecular weight of the gas;

at a second temperature and pressure state of the gas mixture: measuring the speed of sound in the gas mixture, determining the constant values for the gas mixture from the database, and substituting these values into the model equation, thereby obtaining a second equation for the molecular weight of the gas;

at a third temperature and pressure state of the gas mixture: measuring the speed of sound in the gas mixture, determining the constant values for the gas mixture from the database, and substituting these values into the model equation, thereby obtaining a third equation for the molecular weight of the gas; and solving the three equations for the diluent concentrations of the gas.

2. The method of claim 1, wherein at least one of the states is standard temperature and pressure.

3. The method of claim 1, wherein the model equation is expressed as:

$$MW=(A+B/S+C/S^2)*(1+D*X_{CO2}+E*X_{N2}).$$

4. The method of claim 1, wherein the constant values D and E are further expressed as:

$$D=D_0+D_1/S+D_2/S^2 \text{ and } E=E_0+E_1/S+E_2/S^2.$$

5. The method of claim 1, wherein the constants are determined by storing pre-calculated speed of sound values for the reference gases for a range of temperature and pressure values, and applying statistical methods to the stored values.

6. The method of claim 1, wherein the constants are determined by storing pre-calculated speed of sound values for the reference gases for a range of temperature and pressure values, interpolating the data to determine speed-of sound at a given state, substituting molecular weight, speed of sound, and diluent concentration values into the model equation for each of the reference gases, and solving the resulting system of equations for the constant values.

7. The method of claim 1, wherein the constants are determined by calculating speed of sound values for the reference gases for the measured temperature and pressure values, substituting molecular weight, speed of sound, and diluent concentration values into the model equation for each of the reference gases, and solving the resulting system of equations for the constant values.

8. A method of determining the combined diluent concentrations in a natural gas, comprising the steps of:

storing a database representing a number of reference gas mixtures whose molecular weights and diluent concentrations are known;

modeling the molecular weight of a gas mixture as a function of the speed of sound in the gas mixture, the diluent concentrations, and a set of constant values, thereby obtaining a model equation;

at a first temperature and pressure state of the gas mixture: measuring the speed of sound in the gas mixture, determining the constant values for the gas mixture from the database, and substituting these values into the model equation, thereby obtaining a first equation for the molecular weight of the gas;

at a second temperature and pressure state of the gas mixture: measuring the speed of sound in the gas mixture, determining the constant values for the gas mixture from the database, and substituting these values into the model equation, thereby obtaining a second equation for the molecular weight of the gas;

at a third temperature and pressure state of the gas mixture: measuring the speed of sound in the gas mixture, determining the constant values for the gas mixture from the database, and substituting these values into the model equation, thereby obtaining a third equation for the molecular weight of the gas; and solving the three equations for the combined diluent concentrations of the gas.

9. The method of claim 8, further comprising the steps of measuring the carbon dioxide concentration in the gas and subtracting the carbon dioxide concentration from the combined diluent concentration.

10. A two-channel device for measuring the nitrogen concentration in a subject natural gas, comprising:

a first gas flow channel, having a high pressure valve and a low pressure valve, a bypass valve for bypassing at least one of the pressure valves, a speed of sound sensor, a temperature sensor, and a pressure sensor;

a second gas flow channel, having a high pressure valve and a low pressure valve, a bypass valve for bypassing at least one of the pressure valve, a speed of sound sensor, a temperature sensor, and a pressure sensor;

a carbon dioxide sensor for measuring the carbon dioxide concentration in the gas; and a processing unit for receiving speed of sound measurements from the speed of sound sensors, for receiving temperature and pressure measurements from the temperature and pressure sensors, for receiving the carbon dioxide concentration from the carbon dioxide sensor, for storing reference gas data, and for calculating the nitrogen concentration of the subject natural gas based on the speed of sound measurements, the temperature and pressure measurements, the reference gas data, and the carbon dioxide concentration.

11. The device of claim 10, wherein the processing unit has a look up table for storing pre-calculated speed of sound values for a set of reference gases at a range of temperature and pressure states.

12. The device of claim 10, further comprising a heater for raising the temperature of the gas during sensing by at least one of the speed of sound sensors.

13. A two-channel device for measuring at least one of the diluent concentrations in a natural gas, comprising:

a first gas flow channel, having a high pressure valve and a low pressure valve, a bypass valve for bypassing at least one of the pressure valves, a speed of sound sensor, a temperature sensor, and a pressure sensor;

a second gas flow channel, having a high pressure valve and a low pressure valve, a bypass valve for bypassing at least one of the pressure valves, a speed of sound sensor, a temperature sensor, and a pressure sensor; and a processing unit for receiving speed of sound measurements for the speed of sound sensors, for receiving temperature and pressure measurements from the temperature and pressure sensors, for storing reference gas data, and for calculating at least one diluent concentration of a subject gas based on the speed of sound measurements, the temperature and pressure measurements, and the reference gas data.

14. The device of claim 13, wherein the processing unit has a look up table for storing pre-calculated speed of sound values for a set of reference gases at a range of temperature and pressure states.

15. The device of claim 13, further comprising a heater for raising the temperature of the gas during sensing by at least one of the speed of sound sensors.

* * * * *